United States Patent [19]
Olmstead et al.

[11] Patent Number: 5,488,109
[45] Date of Patent: Jan. 30, 1996

[54] 5-ALKOXY[1,2,4]TRIAZOLO[1,5-C] PYRIMIDINE-2(3H)—THIONE COMPOUNDS AND THEIR USE IN THE PREPARATION OF AND 2-CHLOROSULFONYL-5-ALKOXY[1,2,4] TRIAZOLO[1,5-C]-PYRIMIDINE COMPOUNDS

[75] Inventors: Thomas A. Olmstead, Midland; Michael A. Gonzalez, Sanford; Jon A. Orvik, Midland; Douglas L. Pearson, Midland; James W. Ringer, Midland; Dawn Shiang, Sanford; Jimmy J. Tai; Anne P. Wallin, both of Midland, all of Mich.

[73] Assignee: DowElanco, Indianapolis, Ind.

[21] Appl. No.: 148,790

[22] Filed: Nov. 5, 1993

[51] Int. Cl.$^6$ .................................................. C07D 487/04
[52] U.S. Cl. .................................................. 544/263
[58] Field of Search ........................... 544/263; 504/241

[56] References Cited

U.S. PATENT DOCUMENTS

| | | | |
|---|---|---|---|
| 4,528,288 | 7/1985 | Wade | 544/263 |
| 5,008,396 | 4/1991 | Krauss | 548/263.8 |
| 5,163,995 | 11/1992 | Van Heertum et al. | 544/263 |
| 5,177,206 | 1/1993 | Johnson et al. | 544/263 |
| 5,217,521 | 6/1993 | Durr | 544/263 |

FOREIGN PATENT DOCUMENTS

| | | |
|---|---|---|
| 244948 | 11/1987 | European Pat. Off. . |
| 951652 | 3/1964 | United Kingdom ........... 544/263 |

OTHER PUBLICATIONS

Merck Index, 10th Edition (1983) p. 400.
Brown et al., *Australian Journal of Chemistry*, 31, 2505–2515 (1978).
Brown et al., *Australian Journal of Chemistry*, 32, 2713–2726, (1979).
Broadbent et al., *J. Chem. Soc.*, 1965, 3369–3372.

*Primary Examiner*—Donald G. Daus
*Attorney, Agent, or Firm*—D. Wendell Osbourne

[57] ABSTRACT

2-Chlorosulfonyl-5-alkoxy[1,2,4]triazolo-[1,5-c]pyrimidine compounds, such as 2-chlorosulfonyl-5-ethoxy-7-fluoro[1,2,4]triazolo[1,5-c]pyrimidine, that are useful for the preparation of 5-alkoxy[1,2,4]triazolo [1,5-c]pyrimidine-2-sulfonamide herbicides, were prepared in an improved manner from 5-alkoxy[1,2,4]triazolo [1,5-c]pyrimidine-2(3H)-thione compounds, such as 5-ethoxy-7-fluoro[1,2,4]triazolo [1,5-c]pyrimidine-2(3H)-thione, by oxidation with hydrogen peroxide to obtain novel 2,2'-dithiobis(5-alkoxy[1,2,4]triazolo[1,5-c]pyrimidine) compounds, such as 2,2'-dithiobis (5-ethoxy-7-fluoro[1,2,4]triazolo[1,5-c]pyrimidine), and subsequent chloroxidation of these intermediate compounds.

36 Claims, No Drawings

5-ALKOXY[1,2,4]TRIAZOLO[1,5-C]PYRIMIDINE-2(3H)—THIONE COMPOUNDS AND THEIR USE IN THE PREPARATION OF AND 2-CHLOROSULFONYL-5-ALKOXY[1,2,4]TRIAZOLO[1,5-C]-PYRIMIDINE COMPOUNDS

BACKGROUND OF THE INVENTION

The present invention relates to 5-alkoxy[1,2,4]triazolo[1,5-c]pyrimidine-2(3H)-thione compounds and to a method of use of these compounds for the preparation of 2,2'-dithiobis(5-alkoxy[1,2,4]triazolo[1,5-c]pyrimidine) and 2-chlorosulfonyl-5-alkoxy[1,2,4]triazolo[1,5-c]pyrimidine compounds. It further relates to the 2,2'-dithiobis(5-alkoxy[1,2,4]triazolo[1,5-c]pyrimidine) compounds prepared and the use of these compounds for the preparation of 2-chlorosulfonyl-5-alkoxy[1,2,4]triazolo[1,5-c]pyrimidine compounds.

5-Alkoxy[1,2,4]triazolo[1,5-c]pyrimidine-2-sulfonamide compounds that are potent herbicides are described in U.S. Pat. No. 5,163,995. They are disclosed to be prepared in a multistep process that involves the preparation of 2-chlorosulfonyl-5-alkoxy[1,2,4]triazolo[1,5-c]pyrimidine intermediate compounds by the chloroxidation of the corresponding 2-(benzylthio or $C_2$–$C_4$ alkylthio)-5-alkoxy[1,2,4]triazolo[1,5-c]pyrimidine compounds with chlorine in an aqueous medium and the subsequent condensation of these intermediate compounds with substituted aniline or N-trialkysilylaniline compounds. The yields of the desired herbicidal products are variable, often due to the low yields obtained in the chloroxidation and the impure nature of the 2-chlorosulfonyl-5-alkoxy[1,2,4]triazolo[1,5-c]pyrimidine intermediate compounds obtained. The process, further, creates an excessive amount of waste.

Improved methods of preparing the 2-chlorosulfonyl-5-alkoxy[1,2,4]triazolo[1,5-c]pyrimidine intermediates for 5-alkoxy[1,2,4]triazolo[1,5-c]pyrimidine-2-sulfonamide compounds, for example, methods that give higher yields or higher purities or involve simplified operations, are of great interest.

5-Alkoxy[1,2,4]triazolo[1,5-c]pyrimidine-2(3H)-thione and 2,2'-dithiobis(5-alkoxy[1,2,4]triazolo[1,5-c]pyrimidine) compounds have not been described in the art.

SUMMARY OF THE INVENTION

5-Alkoxy[1,2,4]triazolo[1,5-c]pyrimidine-2(3H)-thione compounds have now been prepared and found to be useful in the preparation 2-chlorosulfonyl-5-alkoxy[1,2,4]triazolo[1,5-c]pyrimidine compounds, either directly or through intermediary 2,2'-dithiobis(5-alkoxy[1,2,4]triazolo[1,5-c]pyrimidine) compounds, and, as a result, are useful for the preparation of 5-alkoxy[1,2,4]triazolo[1,5-c]pyrimidine-2-sulfonamide herbicides. The method of use of these compounds that was found involves a process in which the 5-alkoxy[1,2,4]triazolo[1,5-c]pyrimidine-2(3H)-thione compounds are oxidized to 2,2'-dithiobis(5-alkoxy[1,2,4]triazolo[1,5-c]pyrimidine) compounds with an oxidizing agent and these compounds are subsequently chloroxidized to obtain 2-chlorosulfonyl-5-alkoxy[1,2,4]triazolo[1,5-c]pyrimidine compounds. The resulting process allows for the preparation of N-(substituted phenyl)-5-alkoxy[1,2,4]triazolo[1,5-c]pyrimidine-2-sulfonamide herbicides in a more economical and more readily carried out manner than the previously described process.

The invention includes 5-alkoxy[1,2,4]triazolo[1,5-c]pyrimidine-2(3H)-thione compounds of

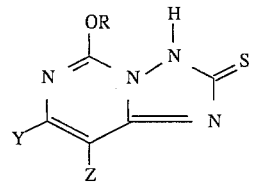

wherein
one of Y and Z represents F, Cl, Br, R', or OR' and the other represents H; and R and R' each independently represents $CH_3$ or $C_2H_5$.

Compounds of Formula I wherein one of Y and Z represents F, Cl, or Br and the other represents H are generally preferred. The fluorinated compounds are usually more preferred but the chlorinated compounds are sometimes more preferred.

The invention further includes a method of use of 5-alkoxy[1,2,4]triazolo[1,5-c]pyrimidine-2(3H)-thione compounds of Formula I:

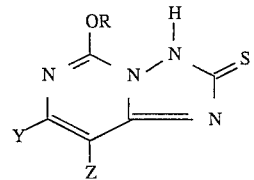

wherein
one of Y and Z represents F, Cl, Br, R', or OR' and the other represents H; and R and R' each independently represents $CH_3$ or $C_2H_5$
which method comprises treating said compound with at least about one equivalent of a suitable oxidizing agent in an inert reaction medium to obtain a 2,2'-dithiobis(5-alkoxy[1,2,4]triazolo[1,5-c]pyrimidine) intermediate compound of Formula II:

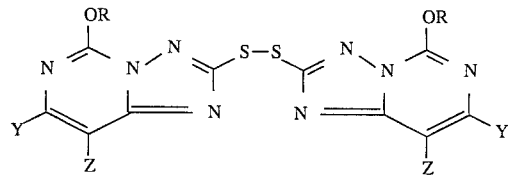

wherein R, Y, and Z are as defined before
and subsequently treating the intermediate with at least about 5 moles of chlorine in a suitable aqueous medium under conditions conducive to chloroxidation to obtain a 2-chlorosulfonyl-5-alkoxy[1,2,4]triazolo[1,5-c]pyrimidine compound of Formula III:

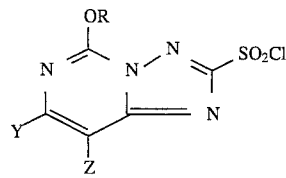

wherein R, Y, and Z are as defined before.

The invention still further includes the 2,2'-dithiobis(5-alkoxy[1,2,4]triazolo[1,5-c]pyrimidine) intermediate compounds of Formula II:

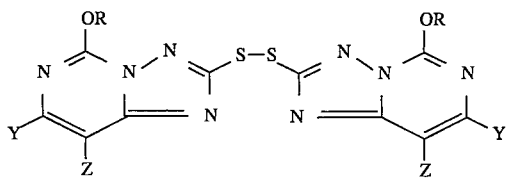
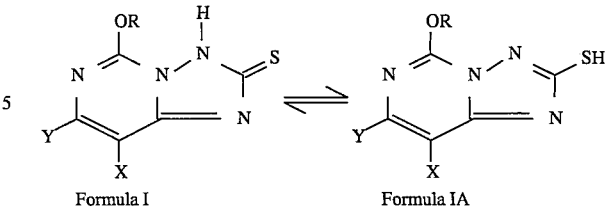

wherein one of Y and Z represents F, Cl, Br, R', or OR' and the other represents H; and R and R' each independently represents $CH_3$ or $C_2H_5$.

Compounds of Formula II wherein one of Y and Z represents F, Cl, or Br and the other represents H are generally preferred. Such compounds wherein one of Y and Z represents F and the other represents H are usually more preferred and those wherein one of Y and Z represents Cl and the other represents H are sometimes more preferred. Compounds of Formula II wherein R represents ethyl are often preferred.

DETAILED DESCRIPTION OF THE INVENTION

The 5-alkoxy[1,2,4]triazolo[1,5-c]pyrimidine-2(3H)-thione compounds of the invention can be characterized as 5-alkoxy[1,2,4]triazolo[1,5-c]pyrimidine-2(3H)-thione compounds wherein the alkoxy group is methoxy or ethoxy and wherein there is a single halogen, alkyl, or alkoxy substituent in the 7- or 8-position. These compounds include compounds of Formula I:

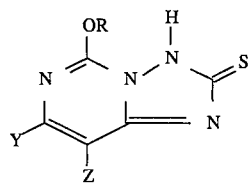

wherein R represents methyl or ethyl and one of Y and Z represents fluorine, chlorine, bromine, methyl, ethyl, methoxy, or ethoxy and the other represents hydrogen.

The fluorinated compounds are typically more preferred but the chlorinated compounds are sometimes more preferred. The more preferred compounds of Formula I include 5-ethoxy-7-(fluoro or chloro)[1,2,4]triazolo[1,5-c]pyrimidine-2(3H)-thione, 5-methoxy-7-(fluoro or chloro)[1,2,4]triazolo[1,5-c]pyrimidine-2(3H)-thione, 5-ethoxy-8-(fluoro or chloro)[1,2,4]triazolo[1,5-c]pyrimidine-2(3H)-thione, and 5-methoxy-8-(fluoro or chloro)[1,2,4]triazolo[1,5-c]pyrimidine-2(3H)-thione.

The compounds of Formula I are named and depicted herein as 2(3H)-thione compounds. They could equally well have been named and depicted as 2-thiol compounds since the two structures are keto-enol type isomers and are in dynamic equilibrium. The keto and enol isomers of the compounds of Formula I are shown below:

The 5-alkoxy[1,2,4]triazolo[1,5-c]pyrimidine-2(3H)-thione compounds of Formula I are not very stable and tend to decompose on standing, even in the solid state. It is preferred to utilize these compounds as intermediates in the synthesis of other, more stable compounds soon after preparing them.

The compounds of Formula I can be prepared by combining a 5-alkoxy-1,2,4-triazolo[4,3-c]pyrimidine-3(2H)-thione compound of Formula IV:

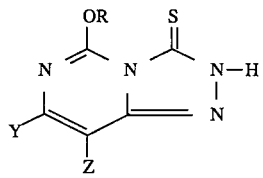

wherein R represents methyl or ethyl and one of Y and Z represents fluoro, chloro, bromo, methyl, ethyl, methoxy, or ethoxy and the other represents hydrogen with at least about one molar equivalent of an alkali metal methoxide or ethoxide in a medium containing methanol or ethanol as the solvent or one of the solvents. The alkali metal alkoxide and the alcohol must be selected so that the 5-alkoxy group of the compound of Formula IV, the alkali metal alkoxide, and the alcohol all have the same alkyl group (methyl or ethyl). If the reagents are not so matched, exchange reactions take place which significantly reduce yields and complicate the recovery procedure.

The alkali metal alkoxides that are employed in the process are the lithium, sodium, and potassium derivatives of methanol and ethanol. At least about one molar equivalent of the alkali metal alkoxide is employed. Ratios of alkali metal alkoxide to the compound of Formula IV of between about 1 and about 2 are typical. Ratios of about 1.03 to about 1.3 are generally preferred. Higher concentrations of alkali metal alkoxide are deleterious to the process.

The reaction medium of the process must contain the appropriate alcohol and may also contain other compatible solvents. Such solvents should be miscible with the alcohol involved, should not cause excessive precipitation of the alkali metal alkoxide, and should not be reactive with any of the reagents or products. Such compatible solvents include acetonitrile, 1,2-dimethoxyethane, N,N-dimethylformamide, dimethyl sulfoxide, and the like. It is preferred that the reaction medium contain less than about 2 percent water. It is more preferred that it contain less than 0.2 percent. The presence of water is responsible for side reactions that destroy the starting material, the product, or both.

The isomerization proceeds well at ambient temperatures and is generally carried out at temperatures of about −10° C. to about 40° C. Temperatures of about 0° C. to about 30° C. are often preferred. The starting materials and products tend to decompose at higher temperatures. The process can be carried out in conventional vessels. The reaction mixture is typically agitated to ensure good mixing.

The rearrangement reaction takes place over the course of a few minutes to a few hours and a solution containing an alkali metal salt of a compound of Formula I is initially obtained. It is preferred that this solution not be allowed to stand for extensive periods of time because the salts of the desired compound of Formula I are not completely stable. The compounds of Formula I, themselves, are obtained by adding sufficient acid to neutralize the medium. Essentially any organic or inorganic protic acid can be used for the acidification. Typically, a cheap and readily available acid having a pKa of less than about 8, such as hydrochloric acid, sulfuric acid, or acetic acid is used. Hydrochloric acid is preferred. Typically, an amount of acid in excess of that required for exact neutralization is added.

The desired compound of Formula I can be recovered by collecting the precipitate that forms upon acidification. Water is typically added after acidification and before the collection to ensure complete precipitation. The recovered product can be collected by filtration or centrifugation and can be dried by conventional means, if desired, provided that excessive heat is avoided. These compounds can be further purified by conventional means, such as by recrystallization, liquid chromatography, and the like.

The 5-alkoxy-1,2,4-triazolo[4,3-c]pyrimidine-3(2H)-thione compounds of Formula IV can be prepared by combining a 2-alkoxy-4-hydrazinopyrimidine compound of Formula V:

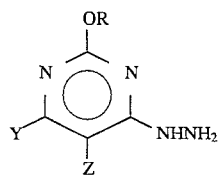

wherein R represents methyl or ethyl and one of Y and Z represents fluoro, chloro, bromo, methyl, ethyl, methoxy, or ethoxy and the other represents hydrogen with at least about one mole of carbon disulfide and, optionally, with a trialkylamine compound of Formula VI:

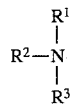

wherein $R^1$, $R^2$, and $R^3$ each independently represents $C_1$–$C_4$ alkyl or benzyl or two of $R^1$, $R^2$, and $R^3$ together represent a moiety of the formula —$(CH_2)_4$—, —$(CH_2)_5$—, or $O(C_2H_4—)_2$, $CH_3N(C_2H_4—)_2$ or all three of $R^1$, $R^2$, and $R^3$ together represent a moiety of the formula $N(C_2H_4—)_3$. The reagents are combined in a suitable inert liquid medium, such as aqueous acetonitrile, at a temperature of about 0° C. to about 40° C. and then at least about one mole of hydrogen peroxide is added at a temperature of about 0° C. to about 40° C. The mixture is typically agitated to assure good mixing. The reaction proceeds quickly with the formation the desired 5-alkoxy-1,2,4-triazolo[4,3-c]pyrimidine-3(2H)-thione compound of Formula IV or, if a trialkylamine compound was added, a trialkylammonium salt thereof. If a trialkylammonium salt is obtained, it can be converted into a compound of Formula IV by adding at least one mole of a strong acid. The compounds of Formula IV obtained can be recovered by adding water to ensure complete precipitation and collecting the precipitate by filtration or centrifugation. The by-product elemental sulfur can be removed by conventional means. The differences in solubility between sulfur and the compounds of Formula IV in aqueous bases (compound of Formula IV soluble and sulfur insoluble) and in carbon disulfide (the opposite) are typically exploited.

The 2-alkoxy-5-substituted-4-hydrazinopyrimidine starting materials of Formula V can be prepared from 2,4-dialkoxy-5-substituted-pyrimidine compounds by treatment with hydrazine and triethylamine. Similarly, the 2-alkoxy-6-substituted-4-hydrazinopyrimidine compounds can be prepared from the corresponding 2-alkoxy-4-halo-6-substituted-pyrimidine compounds by treatment with hydrazine and triethylamine. The reactions are best carried out in water or in a solvent, such as acetonitrile, at a temperature of between about 0° C. about 40° C., using about one mole of triethylamine and slightly in excess of one mole of hydrazine. The desired 2-alkoxy-(5 or 6)-substituted-4-hydrazinopyrimidine compounds of Formula V can be recovered by adding water to promote precipitation and recovering the precipitate by filtration, centrifugation, or extraction. These compounds can, however, often be employed as intermediates without recovery and/or purification.

The process involved in the method of use of the 5-alkoxy[1,2,4]triazolo[1,5-c]pyrimidine-2(3H)-thione compounds of Formula I is an improved method of preparation of 2-chlorosulfonyl-5-alkoxy[1,2,4]triazolo[1,5-c]pyrimidine compounds of Formula III:

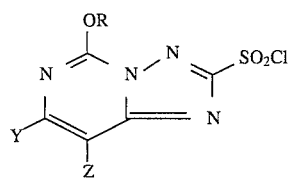

wherein R represents methyl or ethyl and one of Y and Z represents fluoro, chloro, bromo, methyl, ethyl, methoxy or ethoxy, and the other represents hydrogen.

Compounds of Formula III can be described as [1,2,4]triazolo[1,5-c]pyrimidine compounds that possess a chlorosulfonyl moiety in the 2-position, a methoxy or ethoxy moiety in the 5-position and a halogen, alkyl, or alkoxy substituent in the 7- or 8-position. Such compounds wherein one of Y and Z represents fluoro, chloro, or bromo and the other represents hydrogen are usually preferred. Those wherein one of Y and Z represents fluoro and the other represents H are usually more preferred and those wherein one of Y and Z represents chloro and the other represents H are sometimes more preferred.

Specific compounds that can be prepared by the method include 2-chlorosulfonyl-8-fluoro-5-methoxy[1,2,4]triazolo[1,5-c]pyrimidine, 2-chlorosulfonyl-5-ethoxy-7-fluoro[1,2,4]triazolo[1,5-c]pyrimidine, 2-chlorosulfonyl-8-chloro-5-methoxy[1,2,4]triazolo[1,5-c]pyrimidine, and 2-chlorosulfonyl-7-chloro-5-ethoxy[1,2,4]triazolo[1,5-c]pyrimidine.

The compounds of Formula III are known from U.S. Pat. Nos. 5,163,995 and 5,177,206, the appropriate portions of which are hereby incorporated by reference, to be useful for the preparation of herbicidal 5-alkoxy[1,2,4]triazolo[1,5-c]pyrimidine-2-sulfonamide compounds. The compounds of Formula I are coupled with an appropriately substituted aniline or N-trialkylsilylaniline compound in an inert solvent, such as acetonitrile, in the presence of a tertiary amine and/or a catalytic amount of dimethyl sulfoxide.

The process involved in the method of use of the compounds of Formula I can be viewed as a two step procedure involving an oxidation and a chloroxidation reaction. It is carried out by first treating a 5-alkoxy[1,2,4]triazolo[1,5-c]pyrimidine-2(3H)-thione compound of Formula I:

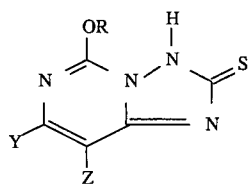

wherein R represents methyl or ethyl and one of Y and Z represents fluoro, chloro, bromo, methyl, ethyl, methoxy, or ethoxy and the other represents hydrogen with suitable oxidizing agent. The compound of Formula I is at least partially dissolved in an inert reaction medium and about one equivalent of the oxidizing agent is added. One equivalent of hydrogen peroxide is 0.5 mole. The reaction takes place rapidly and a 2,2'-dithiobis(5-alkoxy[1,2,4]triazolo[1,5-c]pyrimidine) compound of Formula II:

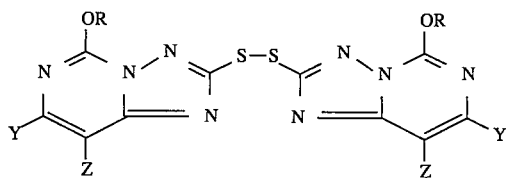

wherein R, Y, and Z are as defined before is formed. The compound of Formula II typically precipitates from the reaction medium and is usually and preferably recovered as a solid.

A suitable oxidizing agent is one that is capable of oxidizing organic thiol and thione compounds to disulfides. Suitable oxidizing agents include hydrogen peroxide, halogens such as bromine, peracids such as peracetic acid, diacyl peroxides such as acetyl peroxide, and alkyl peroxides such as t-butyl peroxide. Hydrogen peroxide is preferred.

It is often preferred to employ hydrogen peroxide as its commercially available 30 percent solution in water as the oxidizing agent. Other forms of hydrogen peroxide, however, can also be employed.

An inert reaction medium for this first step of the process is one in which both the starting material of Formula I and the intermediate of Formula II are reasonably stable, in which the starting material and oxidizing agent are at least partially soluble, and which does not react appreciably with the oxidizing agent or catalyze its decomposition under the reaction conditions. Such reaction media typically contain water as one ingredient. Mixtures of water with methanol, ethanol, 2-propanol, acetonitrile, 1-methoxy-2-propanol, 1,2-dimethoxyethane, and tetrahydrofuran are typical. Aqueous methanol and ethanol are generally preferred. The medium is preferably neutral or slightly acidic. If an acidic medium is employed, hydrochloric acid is typically the acid involved.

The reaction of this first process step takes place readily at ambient temperatures. Temperatures between about −10° C. and about 80° C. are typical and temperatures between about 0° C. and about 40° C. are preferred. The reaction is exothermic and it is preferred to cool the reaction mixture during the reaction. It is further preferred to agitate the reaction mixture and to add the oxidizing agent slowly or in increments.

The compounds of Formula II that are obtained in the first step of the process are typically insoluble in the reaction mixture and precipitate out as they form. Additional water can be added and the reaction mixture can be cooled to ensure complete precipitation. The compounds can be recovered from the reaction medium by filtration or centrifugation. They can be dried by conventional means, if desired, and can be purified by conventional means, such as recrystallization and extraction.

The second step of the process involves a method of use of a compound of Formula II obtained as above, or in any other manner. A compound of Formula II is treated with at least about 5 moles of chlorine in a suitable reaction medium and under conditions conducive to chloroxidation to obtain a compound of Formula III. The compound of Formula III is typically recovered either in the form of a solution in a water immiscible organic solvent or as a solid.

A suitable reaction medium for the second step of the process is one in which the compound of Formula II is at least partially soluble and in which the compound of Formula III has a reasonable degree of stability. Reaction media comprising water and an organic solvent in which the compounds of Formulas II and III are at least partially soluble are often preferred. The organic solvent is, preferably, immiscible with water and the medium comprises at least two phases. Such media include mixtures of water with chlorinated hydrocarbon solvents, such as dichloromethane, chloroform, 1,2-dichloroethane, and perchloroethylene, or with hydrocarbon solvents, such as toluene. An aqueous acid, such as aqueous hydrochloric acid, is often employed as the source of the water in the medium. Mixtures of water and dichloromethane or chloroform are often preferred. Other suitable media include acetonitrile, acetic acid, and formic acid, each either anhydrous or mixed with water. Aqueous hydrochloric acid above about 1N, for example 6.25N hydrochloric acid, can also be employed. Hydrogen chloride is produced as a by-product in the chloroxidation reaction and consequently it is essentially always present and its concentration increases as the reaction proceeds. Typically about 3 to about 20 parts by weight of reaction medium are employed per part of compound of Formula II.

Reaction conditions conducive to chlorinolysis are those under which the desired reaction takes place at a reasonable reaction rate and under which side-reactions are not fostered. Temperatures between about −20° C. and about 40° C. are typical, temperatures between about −10° C. and about 30° C. are usually preferred, and temperatures between about 0° C. and about 15° C. are usually more preferred. The reaction is generally carried out by sparging the chlorine into or just above a mixture containing the compound of Formula II in the suitable reaction medium with agitation and with cooling to maintain the desired temperature. The chlorine is added at a rate such that it disperses rapidly and the temperature is well controlled.

The compounds of Formula III prepared by the process are typically obtained first either as a solution in the organic solvent portion of the reaction medium or as an insoluble solid. When they are obtained in solution, they can be recovered by separating the phases and, optionally, washing the organic phase with water or aqueous acid. The organic solvent can then be removed by evaporation or distillation under reduced pressure or by other conventional means, if desired. The solution can, alternately, be dried by azeotropic distillation, by using a hydroscopic salt, or by other conventional means, and the product used in the form of the resulting dry solution. When the compounds of Formula III are obtained as insoluble solids, they can be recovered by conventional means, such as by filtration or centrifugation and can be dried by conventional means.

It is possible and sometimes preferable to prepare compounds of Formula II from compounds of Formula IV or from compounds of Formula V without recovering the intermediate compounds of Formula I involved. Thus, compounds of Formula I, the use of which is one aspect of this invention, can be produced from compounds of Formula IV as described hereinabove and employed for the production of compounds of Formula II without recovery from the reaction medium employed. Further, compounds of Formula I can be produced from compounds of Formula IV as described hereinabove, which, in turn, were prepared from compounds of Formula V as described hereinabove and employed for the production of compounds of Formula II without recovery of either the compound of Formula IV or the compound of Formula I from the reaction medium employed.

The method of use of the compounds of Formula I for the the preparation of novel 2,2'-dithiobis(5-alkoxy[1,2,4]triazolo[1,5-c]pyrimidine) compounds of Formula II:

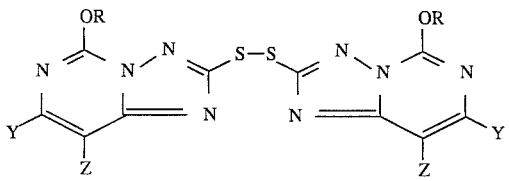

wherein R represents methyl or ethyl and one of Y and Z represents fluoro, chloro, bromo, methyl, ethyl, methoxy, or ethoxy and the other represents hydrogen is another aspect of the invention. The preparation of these compounds is described hereinabove as the first process step in the overall method of utilizing a compound of Formula I to prepare a compound of Formula III.

The invention includes the intermediate 2,2'-dithiobis(5-alkoxy[1,2,4]triazolo[1,5-c]pyrimidine) compounds of Formula II:

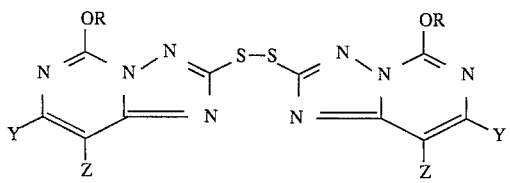

wherein R represents methyl or ethyl and one of Y and Z represents fluoro, chloro, bromo, methyl, ethyl, methoxy, or ethoxy and the other represents hydrogen that are obtained in the method. Compounds of Formula II can be described as symmetrical disulfide compounds possessing a [1,2,4]triazolo[1,5-c]pyrimidine-2-yl moiety attached to each sulfur atom, each of which moieties possesses a methoxy or ethoxy substituent in the 5-position and a single halogen, alkyl, or alkoxy substituent in a 7- or 8-position. The compounds are white or near-white crystalline solids.

Compounds of Formula II wherein one of Y and Z represents fluoro, chloro or bromo and the other represents hydrogen are generally preferred. Those wherein one of Y and Z represents fluoro and the other represents hydrogen are usually more preferred and those wherein one of Y and Z represents chloro and the other represents hydrogen are sometimes more preferred. Compounds of Formula II wherein R represents ethyl are also sometimes preferred.

The preferred compounds of Formula II include 2,2'-dithiobis (8-fluoro-5-methoxy[1,2,4]triazolo[1,5-c]pyrimidine), 2,2'-dithiobis (5-ethoxy-7-fluoro[1,2,4]triazolo[1,5-c]pyrimidine), 2,2'-dithiobis (8-chloro-5-methoxy[1,2,4]triazolo[1,5-c]pyrimidine), and 2,2'-dithiobis (7-chloro-5-ethoxy[1,2,4]triazolo[1,5-c]pyrimidine).

The invention further includes the use of the compounds of Formula II for the preparation of compounds of Formula III. The process involved in this method of use is described hereinabove as the second step in the overall method of converting a compound of Formula I to a compound of Formula III. The method is especially valuable for the use of compounds of Formula II wherein R represents ethyl. The use of compounds of Formula II wherein one of Y and Z represents fluoro and the other represents hydrogen or wherein one of Y and Z represents chloro and the other represents hydrogen are typically preferred.

It is possible to prepare compounds of Formula III from Compounds of Formula I without preparing a compound of Formula II as an intermediate in a distinct reaction step. This method of use of the compounds of Formula I is carried out by treating a compound of Formula I with at least 3 moles of chlorine under reaction conditions conducive to chloroxidation. Reaction conditions conducive to chloroxidation are those under which the desired reaction takes place at a reasonable reaction rate and under which side-reactions are not fostered. Temperatures of about −20° C. and about 40° C. are typical, temperatures between about −10° C. and about 30° C. are preferred, temperatures between about 0° C. and about 15° C. are more preferred. The reaction is generally carried out by sparging the chlorine into or just above a mixture containing the compound of Formula I in a suitable reaction medium with agitation and with cooling to maintain the desired temperature. The chlorine is added at a rate such that it disperses rapidly and the temperature is well controlled.

The following examples are presented to illustrate the invention. They should not be construed as limitations on the claims.

EXAMPLES

1. Preparation of 5-Fluoro-4-hydrazino-2-methoxypyrimidine

5-Fluoro-2,4-dimethoxypyridine (158 g (grams), 1.00 mol), 150 g (3.00 mol) of hydrazine hydrate, and 237 g of methanol were placed in a 1 L (liter) flask and heated to reflux (about 70° C.) for 3.5 hours with stirring. The mixture, which became homogeneous and then heterogeneous again, was then cooled to 0°–5° C. and the solids present were recovered by vacuum filtration, washed with 150 mL (milliliters) of cold methanol, and dried to constant weight. The title compound, which was obtained as colorless needles melting at 188°–189° C., amounted to 151.5 g (96 percent of theory).

NMR data (DMSO-d6) δ: $^1$H: 3.77 (s, 3H), 4.38 (2H), 7.83 (d(J=3.6 Hz), 1H); $^{13}$C: 54.2,137.9 (d($J_{CF}$= 19.6 Hz)), 141.5 (d($J_{CF}$=244.8 Hz)), 154.3 (d($J_{CF}$=13.7 Hz)), 160.6.

2. Preparation of 2-Ethoxy-4-fluoro-6-hydrazinopyrimidine

A mixture of 100 g of 94 percent purity (0.59 mol) 2-ethoxy-4,6-difluoropyrimidine, 275 mL of acetonitrile, and 107 g of water was prepared and cooled to 10° C. To this was added 68 g (0.67 mol) of triethylamine and then 34 g (0.68 mol) of hydrazine hydrate, slowly with stirring and cooling (at 5° to 10° C.). When all of the hydrazine had been added, the mixture was stirred another 15 min with cooling and was then allowed to warm. After a total of 1 hour, the solids that formed were recovered by vacuum filtration and were washed twice with 100 mL portions of water and then with 50 mL of ethanol. The title compound, which was obtained as a white solid melting at 141°–143° C., amounted to 79.7 g (80 percent of theory).

Elemental Analysis for $C_6H_9FN_4O$:

Calc.: %C, 41.9; %H, 5.27; %N, 32.5

Found: %C, 42.2; %H, 5.12; %N, 32.6

3. Preparation of 5-Chloro-4-hydrazino-2-methoxypyrimidine

A solution containing 0.35 g (2.0 mmol) of 5-chloro-2,4-dimethoxypyrimidine and 0.35 g (7.0 mmol) of hydrazine hydrate in 2.9 g of methanol was heated at reflux with stirring for 8 hours. The mixture was then cooled causing a precipitate to form water was added until the precipitation appeared to be complete and the precipitate was then recovered by vacuum filtration and allowed to air dry overnight to obtain 0.23 g (66 percent of theory) of the title compound as a white solid. The product melted at 172°–173° C. after changing crystalline form from needles to cube-like shapes in a phenomenon that appeared to involve sublimation.

NMR data (DMSO-d6) δ: $^1$H: 3.85 (s, 3H), 4.50 (2H), 7.97 (s, 1H), 8.7 (1H); $^{13}$C: 54.17, 105.40, 152.77, 159.39, and 163.39.

4. Preparation of 8-Fluoro-5-methoxy-1,2,4-triazolo[4,3-c]pyrimidine-3(2H)-thione 5-Fluoro-4-hydrazino-2-methoxypyrimidine (15.81 g, 0.100 mol), 47 g of methanol, 10.2 g (0.100 mol) of triethylamine, and 11.4 g (0.15 mol) of carbon disulfide were combined in a 250 mL flask under nitrogen at ambient temperature with stirring to obtain a yellow, heterogeneous mixture. The mixture was cooled to 15° C. with an ice bath. Hydrogen peroxide (12.5 g of 30 percent aqueous, 0.11 mol) was then added by means of a syringe pump, the syringe of which was inserted into the flask through a septum. The addition was made over a 1-hour period with stirring and cooling to maintain the temperature at about 15° C. The mixture was allowed to react and warm for 1 hour and the resulting heterogeneous orange mixture was vacuum filtered to remove the solid sulfur. The filtrate was cooled in an ice bath and acidified with 17.6 mL (0.11 mol) of 6.25N hydrochloric acid diluted with 125 mL of water. The resulting precipitate was recovered by vacuum filtration and dried under reduced pressure to obtain 18.81 g (94 percent of theory) of the title compound as an off-white solid melting at 166° C. with decomposition.

NMR data (DMSO-d6) δ: $^1$H: 4.01 (s, 3H), 7.64 (d(J=2.8 Hz), 1H), 14.5 (brs, 1H); $^{13}$C: 56.00, 125.6 (d($J_{CF}$=22.0 Hz)), 141.6, 141.7 (d($J_{CF}$=41.7 Hz)), 146.0 (d($J_{CF}$=191.0 Hz)), and 161.2.

5. Preparation of 5-Ethoxy-7-fluoro-1,2,4-triazolo[4,3-c]pyrimidine-3(2H)-thione A mixture containing approximately 5.2 g (30 mmol) of 2-ethoxy-4-fluoro-6-hydrazinopyrimidine in a solvent composed of 50 mL of acetonitrile and 15 mL of water was prepared and to this was added 6.4 mL (107 mmol) of carbon disulfide at ambient temperature with stirring. The heterogeneous white mixture became a pale yellow solution after about 10 min and then 3.8 mL of 30 percent aqueous hydrogen peroxide (37 mmol) and 3.2 mL of water were added over a 30-min period with stirring and cooling to hold the temperature at about 25° C. The mixture was allowed to react another 10 min and then 3.22 g (32 mmol) of triethylamine was added and the resulting mixture filtered to remove sulfur. The filtrate was acidified with 10 mL of 3.75N hydrochloric acid (38 mmol). The resulting mixture was filtered to recover the precipitate that formed. This was washed with water and dried to obtain 4.4 g (66 percent of theory) of the title compound of 97 percent purity as a light beige solid melting at 170° C. Considerable product remained in the filtrate.

Elemental Analysis for $C_7H_7FN_4OS$:

Calc.: %C, 39.2; %H, 3.29; %N, 26.2

Found: %C, 39.3; %H, 3.07; %N, 25.9

6. Preparation of 7-Chloro-5-ethoxy-1,2,4-triazolo[4,3-c]pyrimidine-3(2H)-thione A mixture containing 20 g of 93 percent purity (99 mmol) 4-chloro-2-ethoxy-6-hydrazinopyrimidine in a solvent composed of 90 mL of acetonitrile and 26 mL of water was prepared under nitrogen in a 500 mL flask equipped with a condensor and an opening covered by a septum through which the syringe of a syringe pump was inserted. To this was added 11.3 g (148 mmol) of carbon disulfide and, after a 15-min reaction period, 16.7 g of 30 percent aqueous hydrogen peroxide (147 mmol) was added over a 15-min period by means of the syringe with stirring and cooling to hold the temperature at about 25° C. The mixture was allowed to react for another 4 hours and then was cooled to about 0° C. The precipitated product and sulfur by-product were recovered by vacuum filtration and washed with water, a 1:1 mixture of water and acetonitrile, and finally acetonitrile. The wet cake was slurried in 1 L of water at 70° C. and about 600 mL of acetonitrile was added to dissolve the solid. The resulting mixture was gravity filtered and the filtrate was allowed to cool over the weekend. The mixture was further cooled in a refrigerator and the crystals that formed were recovered by vacuum filtration, washed with acetonitrile, and dried to constant weight to obtain 14.1 g (62 percent of theory) of the title compound as an amber solid which decomposed on heating above 187° C.

Elemental Analysis for $C_7H_7Cl_1N_4OS$:

Calc.: %C, 36.4; %H, 3.06; %N, 24.3

Found: %C, 36.4; %H, 2.79; %N, 24.1

7. Preparation of 8-Chloro-5-methoxy-1,2,4-triazolo[4,3-c]pyrimidine-3(2H)-thione 5-Chloro-4-hydrazino-2-methoxypyrimidine (17.45 g, 0.10 mol) and 25 g (0.033 mol) of carbon disulfide were combined in 120 mL of acetonitrile and 30 mL of water at ambient temperature with stirring and 11.4 g (0.10 mol) of 30 percent hydrogen peroxide was added to the resulting mixture with stirring over a 2-hour period. The temperature rose from 20° C. to 48° C. Analysis of the mixture by high pressure liquid chromatography (HPLC) indicated that the reaction was complete. A 79.8 g (47.2 percent of the total) portion of the reaction mixture was diluted with 50 mL of water and the mixture was acidified with hydrochloric acid. The solids present were then recovered by vacuum filtration and dried to obtain 10.15 g of a mixture of the title compound and sulfur. The sulfur was then removed by extracting the solids with 45 g of carbon disulfide to obtain 8.08 g (80 percent of theory) of the title compound as a tan powder. This material was 92 percent pure by HPLC analysis; it decomposed on heating.

NMR data (DMSO-d6) δ: $^1$H: 4.04 (s, 3H), 7.67 (s, 1H), 14.25 (brs, 1H); $^{13}$C: 56.18, 110.08, 140.46, 145.76, 150.11, and 161.32.

8. Preparation of 8-Fluoro-5-methoxy[1,2,4]triazolo[1,5-c]pyrimidine-2(3H)-thione A mixture of 10.01 g (0.050 mol) of 8-fluoro-5-methoxy-1,2,4-triazolo[4,3-c]pyrimidine-3(2H)-thione in 8.6 g of methanol was prepared and cooled with an ice water bath. Sodium methoxide in methanol (32.4 g of 25 percent, 0.15 mol) was added under nitrogen with stirring and cooling. After 2.5 hours, 25.6 mL of ice cold 6.25N aqueous hydrochloric acid was added with stirring to the thick slurry obtained. The resulting mixture was diluted with a little water and the solids were recovered by vacuum filtration and dried under reduced pressure to obtain 8.26 g (83 percent of theory) of the title compound as a colorless powder. The compound melts at 155°–160° C. and then resolidifies and does not remelt up to 230° C.

NMR data (CD$_3$CN) δ: $^1$H: 2.5–3.5 (brs, 1H), 4.21 (s, 3H), 7.92 (d(J=2.1 Hz), 1H); $^{13}$C: 57.4, 118.2, 129.2, 129.5, 143.0, 146.4, 148.7, 149.1, and 163.8.

9. Preparation of 5-Ethoxy-7-fluoro[1,2,4]triazolo[1,5-c]pyrimidine-2(3H)-thione A mixture of 5.8 g (26 mmol) of 5-ethoxy-7-fluoro-1,2,4-triazolo[4,3-c]pyrimidine-3(2H)-thione in 50 mL of absolute ethanol was prepared and to this was added at 0° C. with vigorous stirring and cooling 12.2 mL (33 mmol) of 21 weight percent sodium ethoxide in ethanol. A mildly exothermic reaction took place and the mixture changed from a suspension to a plum colored solution. The mixture was stirred at below 10° C. for 2.25 hours to complete the reaction. It was then acidified with 25 mL of 1.25N hydrochloric acid, stirred at −10° C. for 30 min, and filtered to recover the precipitate that formed. The precipitate was washed with 10 mL of cold water and dried to obtain 3.3 g (60 percent of theory) of the title compound of 98 percent purity. A second crop amounting to 1.7 g of 60 percent purity material (19 percent of theory) was obtained from the filtrate. The title compound melts at 83.5° C. to 86.5° C. and is a white solid.

NMR data (CDCl$_3$) δ: $^1$H: 1.58 (t, 3H), 4.52 (s, 2H), 4,75 (q, 2H), 7.28 (m, 3H), 7.45 (d, 2H).

The identity of the compound was further demonstrated by converting it into 2-benzylthio-5-ethoxy-7-fluoro[1,2,4]triazolo[1,5-c]pyrimidine, melting at 78°–82° C., by treatment with benzyl chloride.

10. Preparation of 8-Chloro-5-methoxy[1,2,4]triazolo [1,5-c]pyrimidine-2(3H)-thione 8-Chloro-5-methoxy-1,2,4-triazolo[4,3-c]-pyrimidine-3(2H)-thione (0.215 g, 1.00 mmol) was mixed with 2.0 g of dry methanol and to this mixture was added, in increments with stirring at ambient temperature, 0.26 g (1.2 mmol) of commercial 25 percent sodium methoxide in methanol. After a 35-min reaction period, the mixture was acidified with aqueous hydrochloric acid and diluted with water. The precipitate that formed was recovered by filtration and dried to obtain 0.168 g of the title compound in 97 percent purity as determined by HPLC (76 percent of theory) as a cream colored solid. The compound can be recrystallized from a mixture of methanol and water; it decomposes, but does not melt up to 250° C.

NMR data (CDCl$_3$) δ: $^1$H: 4.28 (s, 3H), 7.93 (s, 1H) over 14 (not observed); $^{13}$C: 56.0, 112.0, 142.1, 148.0, 153.5, and 163.0.

The identity of the product was further demonstrated by converting it into 2-benzylthio-8-chloro-5-methoxy[1,2,4]triazolo[1,5-c]pyrimidine, a compound known in U.S. Pat. No. 5,163,995, by treatment with benzyl chloride.

11. Preparation of 2,2'-Dithiobis(8-fluoro-5-methoxy[1,2,4]triazolo[1,5-c]pyrimidine)

A heterogeneous mixture composed of 76.0 g (0.380 mol) of 8-fluoro-5-methoxy[1,2,4]triazolo[1,5-c]pyrimidine-2(3H)-thione and 400 g of methanol at 24° C. was prepared and 45.3 g (0.400 mol) of ice cold 30 percent by weight hydrogen peroxide solution was added with stirring. An exothermic reaction took place raising the temperature to 43° C. The mixture was allowed to react for about 75 min and then another 13.0 g (0.115 mol) of ice cold 30 percent by weight hydrogen peroxide solution was added with stirring. The mixture was allowed to react for another 30 min and then the solids present were recovered by vacuum filtration. These solids were dried and were then slurried with methanol. The slurry was heated to reflux, cooled to 35°–45° C., and filtered to recover the insoluble solids. The solids were dried under reduced pressure at 40° C. to obtain 61.9 g of the title compound (80 percent of theory) as an off-white solid. The compound is a white powder melting at 201°–208° C. (dec.).

NMR data (DMSO-d6) δ: $^1$H: 4.16 (s, 3H), 8.21 (d(J=2.1 Hz), 1H).

12. Preparation of 2,2'-Dithiobis(5-ethoxy-7-fluoro[1,2,4]triazolo[1,5-c]pyrimidine)

A solution of 2.9 g (13.5 mmol) of 5-ethoxy-7-fluoro[1,2,4] triazolo[1,5-c]pyrimidine-2(3H)-thione in 30 mL of acetonitrile was prepared and 0.80 mL (7.8 mmol) of 30 percent hydrogen peroxide was added at ambient temperature with stirring under nitrogen. The temperature rose from 21° to 34° C. The mixture was allowed to react for about 1 hour and then 15 mL of water was added and the mixture was cooled to −5° C. The precipitate that formed was recovered by vacuum filtration, washed with two 10 mL portions of a 1:1 mixture of water and acetonitrile at 5° C., and dried to obtain 2.7 g (93 percent of theory) of the title compound as a light beige powder melting at 215°–216° C.

Elemental Analysis for $C_{14}H_{12}F_2N_8O_2S_2$:
Calc.: %C, 39.4; %H, 2.83; %N, 26.3
Found: %C, 39.6; %H, 2.75; %N, 25.9.

13. Preparation of 2,2'-Dithiobis(5-ethoxy-7-fluoro[1,2,4]triazolo[1,5-c]pyrimidine) From 5-Ethoxy-7-fluoro-1,2,4-triazolo[4,3-c]pyrimidine-3(2H)-thione Procedure A: A mixture of 167 g (0.76 mol) of 5-ethoxy-7-fluoro[1,2,4] triazolo[4,3-c]pyrimidine-3(2H)-thione and 1.67 L of toluene denatured absolute ethanol was prepared and to this was added 331 mL (0.887 mol) of 30 percent sodium ethoxide in ethanol at 0° C. with vigorous stirring and cooling. The reaction proceeded with a small exotherm and the heterogeneous light beige mixture became a plum colored solution. This solution was maintained at a temperature of between 5° C. and 10° C. for 2.25 hours and was then acidified with 150 mL of 6.25N hydrochloric acid diluted with 685 mL of water. The resulting mixture was allowed to warm to ambient temperature (23° C.) and then 43.4 mL of 30 percent aqueous hydrogen peroxide (0.43 mole) was added with stirring. The temperature rose to 33° C. and after 30 min all of the thione starting material was consumed as determined by HPLC. The mixture was cooled to 20° C. and the title compound, which precipitated, was recovered by filtration and washed at 5° C. with two 600 mL portions of water and then 350 mL of 50 percent aqueous ethanol. The white solid obtained was dried under reduced pressure at 35° C. to obtain 154 g of the title compound of about 90 percent purity as estimated by HPLC (86 percent of theory).

Procedure B: A solid mixture that is 68 percent pure by analysis and contains 1.89 parts of 5-ethoxy-7-fluoro-1,2,4-triazolo[4,3-c] pyrimidine-3(2H)-thione along with sulfur, less than 2 percent water, and some acetonitrile is diluted with 8.61 parts of absolute ethanol and the mixture is cooled to 10° C. A 21 percent sodium ethoxide by weight in ethanol solution (3.21 parts) is added with stirring and, after a few minutes, the mixture is filtered to remove the sulfur, retaining the filtrate. The sulfur is washed with 0.484 parts of absolute ethanol and the filtered wash ethanol is added to the filtrate. The filtrate mixture is allowed to react at 10° C. until isomerization is complete. The mixture is then acidified with 1.16 parts of 37 percent aqueous hydrochloric acid with stirring and cooling to keep the temperature below 25° C. A 30 percent by weight solution of hydrogen peroxide in water (0.602 parts) is added slowly with stirring and cooling to keep the temperature below 30° C. and the mixture is stirred an additional 30 min after the addition is complete. The precipitate that forms is recovered by filtration in a reduced pressure apparatus and is washed with 3.40 parts of ethanol and 8.70 parts of water to obtain the title compound as a water-wet solid.

14. Preparation of 2,2'-Dithiobis(5-ethoxy-7-fluoro [1,2,4] triazolo[1,5-c]pyrimidine) From 4,6-Difluoro-2-ethoxypyrimidine A mixture consisting of 32.7 g (0.202 mol) of 2-ethoxy-4,6-difluoroethoxypyrimidine, 59 g of acetonitrile, and 36 g of water was prepared in a reaction vessel and the mixture was stirred under nitrogen and cooled to about 5° C. To this was added 21.3 g (0.208 mol) of triethylamine and then 10.6 g (0.208 mol) of hydrazine monohydrate with stirring and cooling at a rate that maintained the reaction temperature at less than 15° C. After all of the hydrazine monohydrate had been added and the exotherm had subsided, the mixture was allowed to warm to ambient temperature to complete the reaction. A solution containing about 32.7 g (0.202 mol) of 2-ethoxy-4-fluoro-6-hydrazinopyrimidine in approximately 95 g of aqueous acetonitrile was obtained.

The solution of 2-ethoxy-4-fluoro-6-hydrazinopyrimidine in aqueous acetonitrile obtained above was placed into a reaction vessel and 23.1 g (0.303 mol) of carbon disulfide was added with stirring under nitrogen. After about 15 min, 23.8 g (0.210 mol) of 30 percent by weight aqueous hydrogen peroxide was added with stirring and cooling to hold the temperature at about 25°–30° C. A precipitate formed. The mixture was allowed to react for about 1 hour and was then cooled to 0° C. It was then filtered to recover the precipitate. The precipitate was washed first with two 75 mL portions of cold water to remove impurities and then with two 50 mL portions of cold acetonitrile to remove water. The 48.7 g of solid material obtained was determined to be 71 percent 5-ethoxy-7-fluoro-1,2,4-triazolo-[4,3-c]pyrimidine-3(2H)-thione by HPLC (35 g, 80 percent of theory) and to contain less than 2 percent water by Karl Fischer titration. Elemental sulfur by-product was the major contaminant.

The 48.7 g (0.16 mol) of 5-ethoxy-7-fluoro-1,2,4-triazolo [4,3-c] pyrimidine-3(2H)-thione as a 71 percent mixture with sulfur and acetonitrile obtained above was combined with 150 g of dry ethanol and the mixture was cooled to about 0° C. To this was added 67.7 g (0.21 mol) of 21 percent sodium ethoxide in ethanol with cooling and stirring such that the temperature was maintained between 5° and 15° C. The pH of the mixture was about 12. The mixture was filtered to remove the solid, insoluble sulfur and it was washed with 20 g of dry ethanol. The filtrate (including the wash ethanol) was allowed to react at about 7° C. for about another 2 hours and then 21.7 g (0.22 mol) of concentrated hydrochloric acid was added to obtain 5-ethoxy-7-fluoro[1,2,4]triazolo[1,5-c] pyrimidine-2(3H)-thione as a a light beige solid in ethanol.

The mixture of 5-ethoxy-7-fluoro[1,2,4]triazolo[1,5-c] pyrimidine-2(3H)-thione in ethanol obtained above was treated with 22.6 g (0,199 mol) of 30 percent hydrogen peroxide with stirring at ambient temperature. There was a mild exotherm. After a 40 min reaction period, the resulting mixture was filtered to recover the precipitate. This was washed with two 100 mL portions of ethanol and two 100 mL portions of water and dried at 37° C. under reduced pressure to obtain 30.9 g (65 percent of theory from 2-ethoxy-4,6-difluoropyrimidine) of the title compound as a light tan solid of 90 percent purity.

15. Preparation of 2-Chlorosulfonyl-5-ethoxy-7-fluoro[1,2,4] triazolo[1,5-c]pyrimidine From 2,2'-Dithiobis(5 -ethoxy-7-fluoro[1,2,4]triazolo[1,5-c]pyrimidine)

Procedure A: A mixture containing 53.3 g of 88 percent purity (0.11 mol) of 2,2'-dithiobis(5-ethoxy-7-fluoro1,2,4] triazolo[1,5-c]pyrimidine), 483 g of dichloromethane, and 12.0 g of water was prepared and cooled to about 5° C. Chlorine (42.5 g, 0.60 mol) was sparged into this mixture with cooling and stirring over a 2.5-hour period so that the temperature did not rise above about 15° C. Another 37.1 g of water was added during the course of the chlorine addition. The solids originally present became thicker at first and then essentially everything went into solution. The resulting mixture was diluted with about 200 mL of water and the phases were separated. The gold colored organic phase was washed with three 400 mL portions of water, dried over magnesium sulfate, filtered, and concentrated by evaporation under reduced pressure with a bath temperature up to 38° C. The title compound was contained in the residue, which amounted to 59.5 g (96 percent of theory) and was a waxy yellow-gold solid. A 12.66 g portion of this was purified by dissolving it in about 30 mL of dichloromethane, adding about 30 mL of hexane, and cooling. The precipitate that formed was recovered by filtration, dried to obtain 8.15 g of the title compound as a white solid. A 3.16 g second crop was also obtained. The product was identified spectroscopically to be the same compound as that reported in U.S. Pat. No. 5,163,995.

Procedure B: A mixture containing 212.5 g (0.44 mol) of 88 percent purity 2,2'-dithiobis(5-ethoxy-7-fluoro[1,2,4] triazolo[1,5-c]pyrimidine), 1985 g of dichloromethane, and 99.0 g of water was prepared in a reaction flask and cooled to about 5° C. with a water/dry ice bath. A total of 170 g (2.4 mol) of chlorine was sparged into the flask just above the liquid level with cooling and stirring over a 4-hour period so that the temperature did not rise above about 15° C. The solids originally present became thicker at first and then essentially everything went into solution. The resulting mixture was diluted with about 300 g of cold water and 220 g of cold 6.25N hydrochloric acid and the phases were separated. The gold colored organic phase was dried over magnesium sulfate, filtered, concentrated by evaporation under reduced pressure, and further dried in a reduced pressure oven at ambient temperature. The 201.6 g yellow-gold solid residue was 91 percent purity (as determined by HPLC) title compound (74.5 percent of theory).

16. Preparation of 2-Chlorosulfonyl-5-ethoxy-7-fluoro [1,2,4]triazolo[1,5-c]pyrimidine From 5-Ethoxy-7-fluoro [1,2,4] triazolo[1,5-c]pyrimidine-2(3H)-thione A mixture consisting of 3.7 g (17.3 mmol) of 5-ethoxy-7-fluoro[1,2,4]triazolo[1,5-c]pyrimidine-2(3H)-thione, 45 mL of dichloromethane, and 15 mL of water was placed in a three necked flask equipped with a mechanical stirrer, an outlet tube connected to a caustic scrubber, a chlorine inlet sparge tube, and a cooling bath. Compete solution was not attained. Chlorine was sparged into the solution at 0° C. with stirring and cooling until 7.0 g, (99 mmol) was added. The solids all dissolved. The aqueous and organic layers were separated and the organic layer was dried over magnesium sulfate and concentrated by evaporation under reduced pressure to obtain the title compound as a residue. The recovered product, which was an orange solid of approximately 88 percent purity, amounted to 3.6 g (75 percent of theory). The compound was identified spectroscopically to be the same as that reported in U.S. Pat. No. 5,163,995.

What is claimed is:

1. A 5-alkoxy[1,2,4]triazolo[1,5-c]pyrimidine-2(3H)-thione compound of the formula:

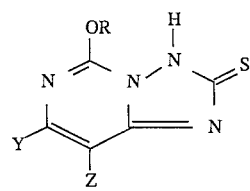

wherein one of Y and Z represents F, Cl, Br, R', or OR' and the other represents H; and R and R' each independently represents CH₃ or C₂H₅.

2. A compound according to claim 1 wherein one of Y and Z represents Cl or F and the other represents H.

3. A compound according to claim 2 which is 8-fluoro-5-methoxy[1,2,4]triazolo[1,5-c]pyrimidine-2(3H)-thione.

4. A compound according to claim 2 which is 5-ethoxy-7-fluoro[1,2,4]triazolo[1,5-c]pyrimidine-2(3H)-thione.

5. A compound according to claim 2 which is 8-chloro-5-methoxy-1,2,4-triazolo[1,5-c]pyrimidine-2(3H)-thione.

6. A method of use of a 5-alkoxy[1,2,4]triazolo[1,5-c]pyrimidine-2(3H)-thione compound of the formula:

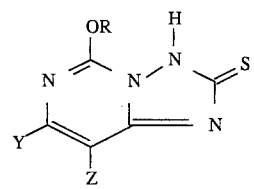

wherein one of Y and Z represents F, Cl, Br, R', or OR' and the other represents H; and R and R' each independently represents CH₃ or C₂H₅ which method comprises treating said compound with at least about one equivalent of an oxidizing agent selected from hydrogen peroxide, a peracid, a diacyl peroxide, and an alkyl peroxide in an inert reaction medium at a temperature between about 0° C. and about 40° C. to obtain a 2,2'-dithiobis(5-alkoxy[1,2,4]triazolo[1,5-c]pyrimidine) intermediate compound of the formula:

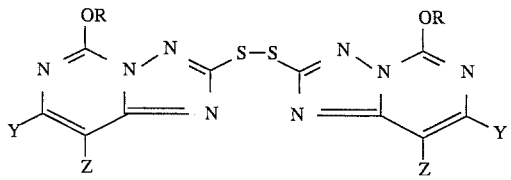

wherein R, Y, and Z are as defined before and subsequently treating the intermediate with at least about 5 moles of chlorine in a reaction medium selected from a mixture of a chlorinated hydrocarbon or hydrocarbon solvent and water, aqueous hydrochloric acid, and anhydrous acetic acid at a temperature of about −10° C. to about 30° C. to effect chloroxidation and to obtain a 2-chlorosulfonyl-5-alkoxy[1,2,4]triazolo[1,5-c]pyrimidine compound of the formula:

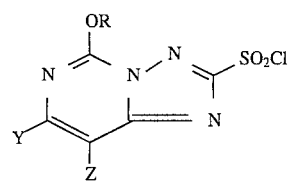

wherein R, Y, and Z are as defined before.

7. A method according to claim 6 wherein the oxidizing agent is hydrogen peroxide.

8. A method according to claim 6 wherein the reaction medium for the oxidation is a mixture of methanol or ethanol and water.

9. A method according to claim 6 wherein the reaction medium for the chloroxidation is a mixture of a methylene chloride or chloroform and water.

10. A method according to claim 6 wherein the reaction medium for the chloroxidation is aqueous hydrochloric acid.

11. A method according to claim 6 wherein the reaction medium for the chloroxidation is anhydrous acetic acid.

12. A method according to claim 6 wherein a 5-alkoxy[1,2,4]triazolo[1,5-c]pyrimidine-2(3H)-thione compound wherein one of Y and Z represents F or Cl and the other represents H is treated.

13. A method according to claim 12 wherein the compound treated is 5-ethoxy-7-fluoro[1,2,4]triazolo [1,5-c]pyrimidine-2(3H)-thione.

14. A method according to claim 12 wherein the compound treated is 8-fluoro-5-methoxy[1,2,4]triazolo [1,5-c]pyrimidine-2(3H)-thione.

15. A method according to claim 12 wherein the compound treated is 8-chloro-5-methoxy[1,2,4]triazolo [1,5-c]pyrimidine-2(3H)-thione.

16. A method of use of a 5-alkoxy[1,2,4]triazolo[1,5-c]pyrimidine-2(3H)-thione compound of the formula:

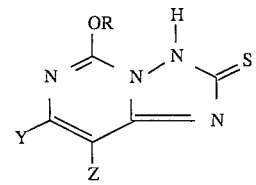

wherein one of Y and Z represents F, Cl, Br, R', or OR' and the other represents H; and R and R' each independently represents CH₃ or C₂H₅ which method comprises treating said compound with at least about one equivalent of an oxidizing agent selected from hydrogen peroxide, a peracid, a diacyl peroxide, and an alkyl peroxide in an inert reaction medium at a temperature between about 0° C. and about 40° C. to obtain a 2,2'-dithiobis(5-alkoxy[1,2,4]triazolo[1,5-c]pyrimidine) intermediate compound of the formula:

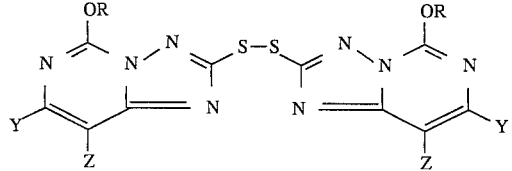

wherein R, Y, and Z are as defined before.

17. A method according to claim 16 wherein the oxidizing agent is hydrogen peroxide.

18. A method according to claim 16 wherein the reaction medium is a mixture of methanol or ethanol and water.

19. A method according to claim 16 wherein in the compound prepared one of Y and Z represents F or Cl and the other represents H.

20. A method according to claim 19 wherein the compound prepared is 2,2'-dithiobis (5-ethoxy-7-fluoro[1,2,4]triazolo[1,5-c]pyrimidine ).

21. A method according to claim 19 wherein the compound prepared is 2,2'-dithiobis(8-fluoro-5-methoxy[1,2,4]triazolo[1,5-c]pyrimidine).

22. A method according to claim 19 wherein the compound prepared is 2,2'-dithiobis(8-chloro-5-methoxy[1,2,4]triazolo[1,5-c]pyrimidine).

23. A 2,2'-dithiobis(5-alkoxy[1,2,4]triazolo[1,5-c]pyrimidine) compound of the formula:

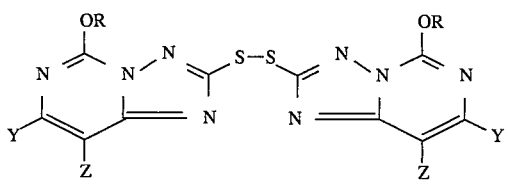

wherein one of Y and Z represents F, Cl, Br, R', or OR' and the other represents H; and R and R' each independently represents $CH_3$ or $C_2H_5$.

24. A compound according to claim 23 wherein one of Y and Z represents F or Cl and the other represents H.

25. A compound according to claim 24 which is 2,2'-dithiobis (5-ethoxy-7- fluoro[1,2,4]triazolo[1,5-c]pyrimidine).

26. A compound according to claim 24 which is 2,2'-dithiobis(8-fluoro-5-methoxy[1,2,4]triazolo[1,5-c]pyrimidine).

27. A compound according to claim 24 which is 2,2'-dithiobis (8-chloro-5-methoxy[1,2,4]triazolo[1,5-c]pyrimidine).

28. A method of use of a 2,2'-dithiobis(5-alkoxy[1,2,4]triazolo[1,5-c]pyrimidine) compound of the formula:

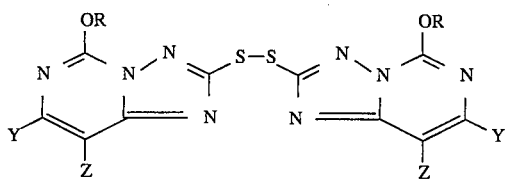

wherein one of Y and Z represents F, Cl, Br, R', or OR' and the other represents H; and R and R' each independently represents $CH_3$ or $C_2H_5$ which method comprises treating the compound with at least about 5 moles of chlorine in a reaction medium selected from a mixture of a chlorinated hydrocarbon or hydrocarbon solvent and water, aqueous hydrochloric acid, and anhydrous acetic acid a temperature of about −10° C. to about 30° C. to effect chloroxidation and to obtain a 2-chlorosulfonyl-5-alkoxy[1,2,4]triazolo[1,5-c]pyrimidine compound of the formula:

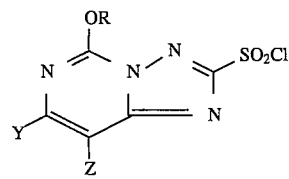

wherein R, Y, and Z are as defined before.

29. A method according to claim 28 wherein the reaction medium is a mixture of methylene chloride or chloroform and water.

30. A method according to claim 28 wherein the reaction medium is aqueous hydrochloric acid.

31. A method according to claim 28 wherein the reaction medium is anhydrous acetic acid.

32. A method according to claim 28 wherein a 2,2-dithiobis(5-alkoxy[1,2,4]triazolo[1,5-c]pyrimidine) compound wherein one of Y and Z represents F or Cl and the other represents H is treated.

33. A method according to claim 28 wherein a 2,2-dithiobis(5-alkoxy[1,2,4]triazolo[1,5-c]pyrimidine) compound wherein R represents ethyl is treated.

34. A method according to claim 32 wherein the compound treated is 2,2-dithiobis(5-ethoxy-7-fluoro[1,2,4]triazolo[1,5-c]pyrimidine).

35. A method according to claim 32 wherein the compound treated is 2,2-dithiobis(8-fluoro-5-methoxy[1,2,4]triazolo[1,5-c]pyrimidine).

36. A method according to claim 32 wherein the compound treated is 2,2-dithiobis(8-chloro-5-methoxy[1,2,4]triazolo[1,5-c]pyrimidine).

* * * * *

UNITED STATES PATENT AND TRADEMARK OFFICE
CERTIFICATE OF CORRECTION

PATENT NO. : 5,488,109
DATED : Jan. 30, 1996
INVENTOR(S) : Thomas A. Olmstead, Michael A. Gonzalez, Jon A. Orvik; Douglas L. Pearson; James W. Ringer; Dawn Shiang; Jimmy J. Tai; Ann P. Wallin It is certified that error appears in the above-indentified patent and that said Letters Patent is hereby corrected as shown below:

title page
Item [54] and col. 1, line 4,
Incorrect Title, "5-ALKOXY[1,2,4]TRIAZOLO[1,5-C]
PYRIMIDINE-2(3H)-THIONE COMPOUNDS
AND THEIR USE IN THE PREPARATION OF
AND
2-CHLOROSULFONYL-5-ALKOXY[1,2,4]
TRIAZOLO[1,5-C]-PYRIMIDINE
COMPOUNDS"

Should read -- 5-ALKOXY[1,2,4]TRIAZOLO[1,5-C]PYRIMIDINE-2(3H)-THIONE
COMPOUNDS AND THEIR USE IN THE PREPARATION OF
2,2'-DITHIOBIS(5-ALKOXY[1,2,4]TRIAZOLO[1,5-C]PYRIMIDINE)
AND 2-CHLOROSULFONYL-5-ALKOXY[1,2,4]TRIAZOLO[1,5-C]-
PYRIMIDINE COMPOUNDS Signed and Sealed this Seventh Day of May, 1996

Attest:

BRUCE LEHMAN

Attesting Officer     Commissioner of Patents and Trademarks